US00PP30869P2

(12) United States Plant Patent
Kerley et al.

(10) Patent No.: US PP30,869 P2
(45) Date of Patent: Sep. 3, 2019

(54) ***CALENDULA* PLANT NAMED 'KERCALDIYELL'**

(50) Latin Name: *Calendula hybrida*
Varietal Denomination: Kercaldiyell

(71) Applicants: Timothy Edward Kerley, Willingham (GB); Sarah Elisabeth Kerley, Willingham (GB); David William Kerley, Over (GB); Priscilla Grace Kerley, Over (GB)

(72) Inventors: Timothy Edward Kerley, Willingham (GB); Sarah Elisabeth Kerley, Willingham (GB); David William Kerley, Over (GB); Priscilla Grace Kerley, Over (GB)

( * ) Notice: Subject to any disclaimer, the term of this patent is extended or adjusted under 35 U.S.C. 154(b) by 0 days.

(21) Appl. No.: 15/998,171

(22) Filed: Jul. 12, 2018

(51) Int. Cl.
*A01H 5/02* (2018.01)

(52) U.S. Cl.
USPC ..... Plt./263.1
CPC ..... *A01H 5/02* (2013.01)

(58) Field of Classification Search
USPC ..... Plt./263.1
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Calendula* plant named 'Kercaldiyell', characterized by its compact, upright to outwardly spreading and mounding plant habit; moderately vigorous growth habit; freely branching habit; freely and continuously flowering habit; long flowering period; large double-type inflorescences with bright yellow-colored ray florets; and good container and landscape performance.

2 Drawing Sheets

Botanical designation: *Calendula hybrida*.
Cultivar denomination: 'KERCALDIYELL'.

BACKGROUND OF THE INVENTION

The present invention relates to a new and distinct cultivar of *Calendula* plant, botanically known as *Calendula hybrida* and hereinafter referred to by the name 'Kercaldiyell'.

The new *Calendula* plant is a product of a planned breeding program conducted by the Inventors in Cambridge, United Kingdom. The objective of the breeding program is to create new uniform *Calendula* plants that flower continuously for a long period of time and have good container and landscape performance.

The new *Calendula* plant originated from a cross-pollination of a proprietary selection of *Calendula hybrida* identified as code number 13-5-8, not patented, as the female, or seed, parent with a proprietary selection of *Calendula hybrida* identified as code number 13-51-7, not patented, as the male, or pollen, parent in 2014. The new *Calendula* plant was discovered and selected by the Inventors as a single flowering plant from within the progeny of the stated cross-pollination in a controlled greenhouse environment in Cambridge, United Kingdom in July, 2015.

Asexual reproduction of the new *Calendula* plant by vegetative tip cuttings in a controlled greenhouse environment in Cambridge, United Kingdom since August, 2015 has shown that the unique features of this new *Calendula* plant are stable and reproduced true to type in successive generations.

SUMMARY OF THE INVENTION

Plants of the new *Calendula* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of the new *Calendula*. These characteristics in combination distinguish 'Kercaldiyell' as a new and distinct *Calendula* plant:

1. Compact, upright to outwardly spreading and mounding plant habit.
2. Moderately vigorous growth habit.
3. Freely branching habit.
4. Freely and continuously flowering habit.
5. Long flowering period.
6. Large double-type inflorescences with bright yellow-colored ray florets.
7. Good container and landscape performance.

Plants of the new *Calendula* differ primarily from plants of the female parent selection in the following characteristics:

1. Plants of the new *Calendula* flower earlier in the spring than plants of the female parent selection.
2. Plants of the new *Calendula* have smaller inflorescences than plants of the female parent selection.
3. Plants of the new *Calendula* have double-type inflorescences whereas plants of the female parent selection have double and semi-double-type inflorescences.
4. Plants of the new *Calendula* have not been observed to set seed whereas plants of the female parent selection have abundant seed set.

Plants of the new *Calendula* differ primarily from plants of the male parent selection in the following characteristics:

1. Plants of the new *Calendula* are more freely flowering than plants of the male parent selection.

2. Plants of the new *Calendula* have smaller inflorescences than plants of the male parent selection.
3. Plants of the new *Calendula* have longer peduncles than plants of the male parent selection.

Plants of the new *Calendula* also can be compared to plants of *Calendula hybrida* 'Kercalsun', not patented. In side-by-side comparisons, plants of the new *Calendula* differ primarily from plants of 'Kercalsun' in the following characteristics:

1. Plants of the new *Calendula* are more freely branching than plants of 'Kercalsun'.
2. Ray florets of plants of the new *Calendula* are narrower than ray florets of plants of 'Kercalsun'.
3. Plants of the new *Calendula* produce more terminal cuttings than plants of 'Kercalsun'.

Plants of the new *Calendula* can be compared to plants of *Calendula offincinalis* 'Cheers Yellow', not patented. In side-by-side comparisons, plants of the new *Calendula* differ primarily from plants of 'Cheers Yellow' in the following characteristics:

1. Plants of the new *Calendula* are more outwardly spreading and mounding than and not as upright as plants of 'Cheers Yellow'.
2. Plants of the new *Calendula* and 'Cheers Yellow' differ in inflorescence form as plants of 'Cheers Yellow' have semi-double and single-type inflorescences.
3. Plants of the new *Calendula* have been observed to be resistant to Powdery Mildew (*Erysiphe* and/or *Sphaerotheca* species) whereas plants of 'Cheers Yellow' are not resistant to Powdery Mildew.

BRIEF DESCRIPTION OF THE PHOTOGRAPHS

The accompanying photographs illustrate the overall appearance of the new *Calendula* plant showing the colors as true as it is reasonably possible to obtain in colored reproductions of this type. Colors in the photographs may differ slightly from the color values cited in the detailed botanical description which accurately describe the colors of the new *Calendula* plant.

The photograph on the first sheet is a side perspective view of a typical flowering plant of 'Kercaldiyell' grown in a container.

The photograph on the second sheet is a close-up view of a typical flowering plant of 'Kercaldiyell'.

DETAILED BOTANICAL DESCRIPTION

The aforementioned photographs and following observations and measurements describe plants grown during the spring in 7.5-liter containers in a glass-covered greenhouse in Cambridge, United Kingdom and under cultural practices typical of commercial *Calendula* production. Plants were twelve weeks from planting rooted cuttings when the photographs were taken and 16 weeks from planting rooted cuttings when the description was taken. In the following description, color references are made to The Royal Horticultural Society Colour Chart, 2007 Edition, except where general terms of ordinary dictionary significance are used.

Botanical classification: *Calendula hybrida* 'Kercaldiyell'.

Parentage:

*Female, or seed, parent*.—Proprietary selection of *Calendula hybrida* identified as code number 13-5-8, not patented.

*Male, or pollen, parent*.—Proprietary selection of *Calendula hybrida* identified as code number 13-51-7, not patented.

Propagation:

*Type*.—By vegetative tip cuttings.

*Time to initiate roots, summer*.—About seven days at soil temperatures about 21° C.

*Time to initiate roots, winter*.—About ten days at soil temperatures about 21° C.

*Time to produce a rooted young plant, summer*.—About three weeks at soil temperatures about 21° C.

*Time to produce a rooted young plant, winter*.—About four weeks at soil temperatures about 21° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Compact, upright to somewhat outwardly spreading and mounding plant habit; moderately vigorous growth habit and moderate growth rate.

*Branching habit*.—Freely branching habit with about four to five primary stems each with about four to six secondary lateral branches; dense and bushy appearance.

*Plant height*.—About 27 cm.

*Plant diameter or spread*.—About 33 cm.

*Lateral branches*.—Length: About 24 cm. Diameter: About 8 mm. Internode length: About 2.7 cm. Strength: Strong. Aspect: Main stems, mostly upright; lateral stems about 45° from main stems. Texture and luster: Pubescent, ridged; matte. Color: Close to 146C to 146D.

Leaf description:

*Arrangement*.—Alternate, simple; sessile.

*Length*.—About 9.8 cm.

*Width*.—About 3.4 cm.

*Shape*.—Oblanceolate.

*Apex*.—Acute.

*Base*.—Truncate.

*Margin*.—Entire.

*Texture and luster, upper and lower surfaces*.—Pubescent; matte.

*Venation pattern*.—Pinnate.

*Color*.—Developing leaves, upper surface: Close to 137B. Developing leaves, lower surface: Close to 147B. Fully expanded leaves, upper surface: Close to 146A; venation, close to 146B. Fully expanded leaves, lower surface: Close to 146B; venation, close to 146D.

Inflorescence description:

*Appearance*.—Double-type inflorescences developing on terminal and axillary peduncles; inflorescences with numerous ray forest and no disc florets; inflorescences positioned on strong peduncles; inflorescences face mostly upright to outwardly.

*Flowering habit*.—Freely flowering habit with two to three open inflorescences per each lateral branch.

*Fragrance*.—None detected.

*Flowering response*.—Early flowering habit, plants begin flowering about eight weeks after planting in Cambridge, United Kingdom.

*Natural flowering season*.—Long flowering period, plants flower continuously from spring until frost in temperate regions; in Cambridge, United Kingdom, plants flower from March until November.

*Inflorescence longevity*.—Depending on actual temperature, inflorescences last about seven to ten days on the plant; inflorescences persistent.

*Inflorescence buds*.—Height: About 1.3 cm. Diameter: About 1 cm. Shape: Ovoid. Texture and luster: Slightly pubescent; matte. Color: Close to 137B; distally, close to 9A and apices, close to 166A.

*Inflorescence diameter*.—About 5.7 cm.

*Inflorescence height* (*depth*).—About 1.5 cm.

*Receptacle diameter*.—About 8 mm.

*Receptacle height*.—About 3 mm.

*Receptacle color*.—Close to 145B.

*Ray florets*.—Number of ray florets per inflorescence: About 126 arranged in about five to six whorls. Length: About 3 cm. Width: About 3 mm. Shape: Oblanceolate. Apex: Acute to slightly fimbriate. Base: Narrowly cuneate. Margin: Entire. Aspect: Mostly horizontal, apices reflexing with development. Texture and luster, upper surface: Smooth, glabrous; glossy. Texture and luster, lower surface: Mostly smooth and glabrous, proximally, pubescent; matte. Color: When opening, upper surface: Brighter and slightly darker than 5A; at the apices, tipped with close to 166A to 166B. When opening, lower surface: Brighter and slightly darker than 5A; at the apices, tipped with close to 166B. Fully opened, upper surface: Close to 3A; at the apices, tipped with close to 166A; venation, very faint, close to 175A; color does not fade with development. Fully opened, lower surface: Close to 5A; venation, very faint, close to 166B; color does not fade with development.

*Disc florets*.—To date, disc floret initiation and development have not been observed on inflorescences of plants of the new *Calendula*.

*Phyllaries*.—Quantity per inflorescence and arrangement: About 23 arranged in a single whorl. Length: About 8 mm. Width: About 1 mm. Shape: Oblanceolate. Apex: Acute. Base: Truncate. Margin: Entire. Aspect: When opening, mostly upright; open inflorescences, mostly horizontal. Texture and luster, upper surface: Smooth, glabrous; glossy. Texture and luster, lower surface: Pubescent; matte. Color, upper surface: Close to 147B; towards the apex, close to 147A. Color, lower surface: Close to 147C; towards the apex, close to 147B.

*Peduncles*.—Length, terminal peduncle: About 4.1 cm. Diameter, terminal peduncle: About 2 mm. Strength: Strong. Aspect: Mostly upright; bending with development. Texture and luster: Slightly pubescent; glossy. Color: Close to 144C to 144D.

*Reproductive organs*.—Androecium: Not observed on ray florets. Gynoecium: Quantity per ray floret: One. Pistil length: About 6 mm. Style length: About 4 mm. Style color: Close to 11A. Stigma shape: Bi-parted. Stigma color: Close to 167B. Ovary color: Close to 144C.

*Seeds and fruits*.—To date, seed and fruit development have not been observed on plants of the new *Calendula*.

Disease & pest resistance: Plants of the new *Calendula* have been observed to be resistant to Powdery Mildew (*Erysiphe* and/or *Sphaerotheca* species). Plants of the new *Calendula* have not been shown to be resistant to pests and other pathogens common to *Calendula* plants.

Garden performance: Plants of the new *Calendula* have been observed to have good garden performance and to tolerate temperatures from about −5° C. to about 30° C.

It is claimed:

1. A new and distinct *Calendula* plant named 'Kercaldi-yell' as illustrated and described.

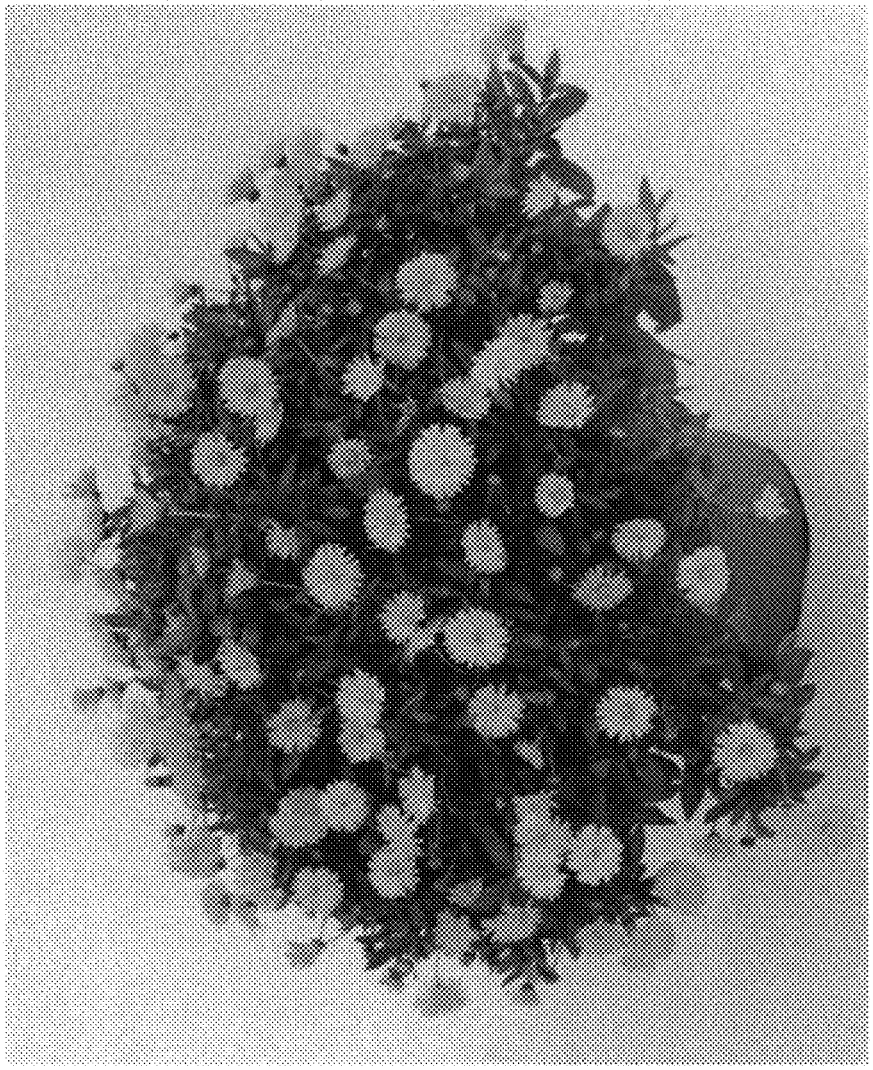

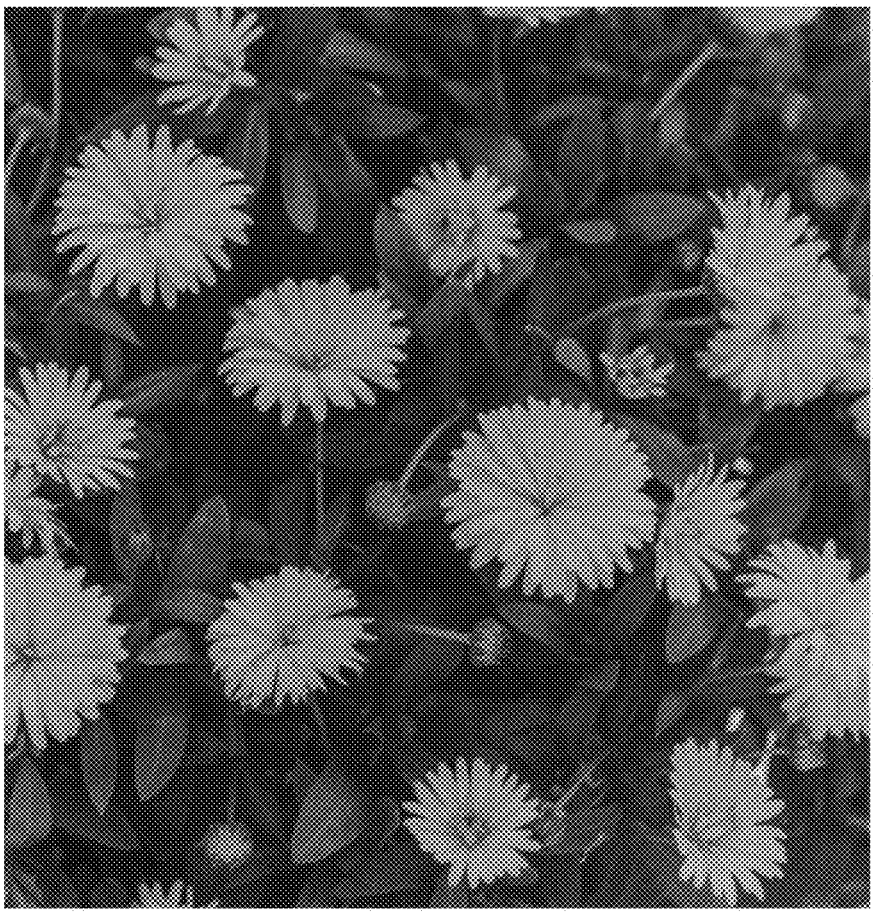

* * * * *